United States Patent [19]

Patil et al.

[11] Patent Number: 4,463,758

[45] Date of Patent: Aug. 7, 1984

[54] COMPUTED TOMOGRAPHY STEREOTACTIC FRAME

[75] Inventors: Arun A. Patil, 1011 Valley View Dr., Minot, N. Dak. 58701; E. Amundson, Minot, N. Dak.

[73] Assignee: Arun A. Patil, Minot, N. Dak.

[21] Appl. No.: 303,408

[22] Filed: Sep. 18, 1981

[51] Int. Cl.³ .................... A61B 19/00; A61B 17/00
[52] U.S. Cl. ..................... 128/303 B; 33/174 D; 378/162; 378/208; 128/630
[58] Field of Search ............... 128/303 B, 653, 660, 128/663, 83; 33/174 D, 191; 269/328, 322, 323; 378/208, 20, 206, 162, 163, 164; 433/55, 56, 68

[56] References Cited

U.S. PATENT DOCUMENTS

| | | | |
|---|---|---|---|
| 2,697,433 | 12/1954 | Zehnder | 128/83 |
| 3,025,608 | 3/1962 | Hendrix | 33/191 |
| 3,061,936 | 11/1962 | Dobbeleer | 128/303 B |
| 3,223,087 | 12/1965 | Vladyka et al. | 33/174 D |
| 3,318,010 | 5/1967 | Mahl | 33/191 |
| 3,357,431 | 12/1967 | Newell | 128/303 B |
| 4,045,678 | 8/1977 | Rickard | 269/328 |
| 4,058,114 | 11/1977 | Soldner | 128/303 B |
| 4,166,459 | 9/1979 | Nightingale | 269/328 |
| 4,243,025 | 1/1981 | Jones | 269/328 |
| 4,256,112 | 3/1981 | Kopf et al. | 269/328 |
| 4,341,220 | 7/1982 | Perry | 128/630 |
| 4,350,159 | 9/1982 | Gouda | 128/303 B |
| 4,360,028 | 11/1982 | Barbier et al. | 128/303 B |

Primary Examiner—Richard J. Apley
Assistant Examiner—Harry J. Macey
Attorney, Agent, or Firm—Zarley, McKee, Thomte, Voorhees & Sease

[57] ABSTRACT

A computed tomography stereostactic frame is disclosed designed for use with a CT Scanner. The frame comprises a platform or support including an area thereon for supporting a patient's head and for maintaining the patient's head in position. An inverted substantially U-shaped frame is selectively movably mounted on the support. A probe holder is selectively movably mounted on either of the leg portions or the base portion of the frame and is designed to permit a twist drill bit or probe to be extended therethrough.

8 Claims, 4 Drawing Figures

COMPUTED TOMOGRAPHY STEREOTACTIC FRAME

BACKGROUND OF THE INVENTION

The technique of computerized or computed tomography was developed in approximately 1972 and involves a diagnostic X-ray system designed for neuroradiological investigations. Different techniques and instrumentations have been provided for computerized tomography to accurately probe deep seated brain lesions. In some instances, the CT Scan is used for guidance and in other instances, the CT Scan is combined with stereotactic techniques.

A principal object of the invention is to provide a unique and simple stereotactic frame which has minimal or no artifact to enable it to be used in combination with a CT Scanner.

A further object of the invention is to provide a stereotactic frame which is convenient to use.

A still further object of the invention is to provide a stereotactic frame including a probe holder means selectively mounted thereon.

A still further object to the invention is to provide a stereotactic frame including a probe holder which may be selectively movably mounted on either of the leg portions or the base portions of an inverted U-shaped frame means which is longitudinally and pivotally mounted on a platform or support designed to support the patient's head thereon.

A still further object of the invention is to provide a stereotactic frame including means for maintaining the patient's head thereon in the proper position.

A still further object of the invention is to provide a stereotactic frame which includes means thereon for aligning the same in the same plane with respect to the head of the patient in which the CT Scan has localized the lesion with the help of the laser beam indicator of the CT Scanner.

These and other objects will be apparent to those skilled in the art.

SUMMARY OF THE INVENTION

Figure 1:
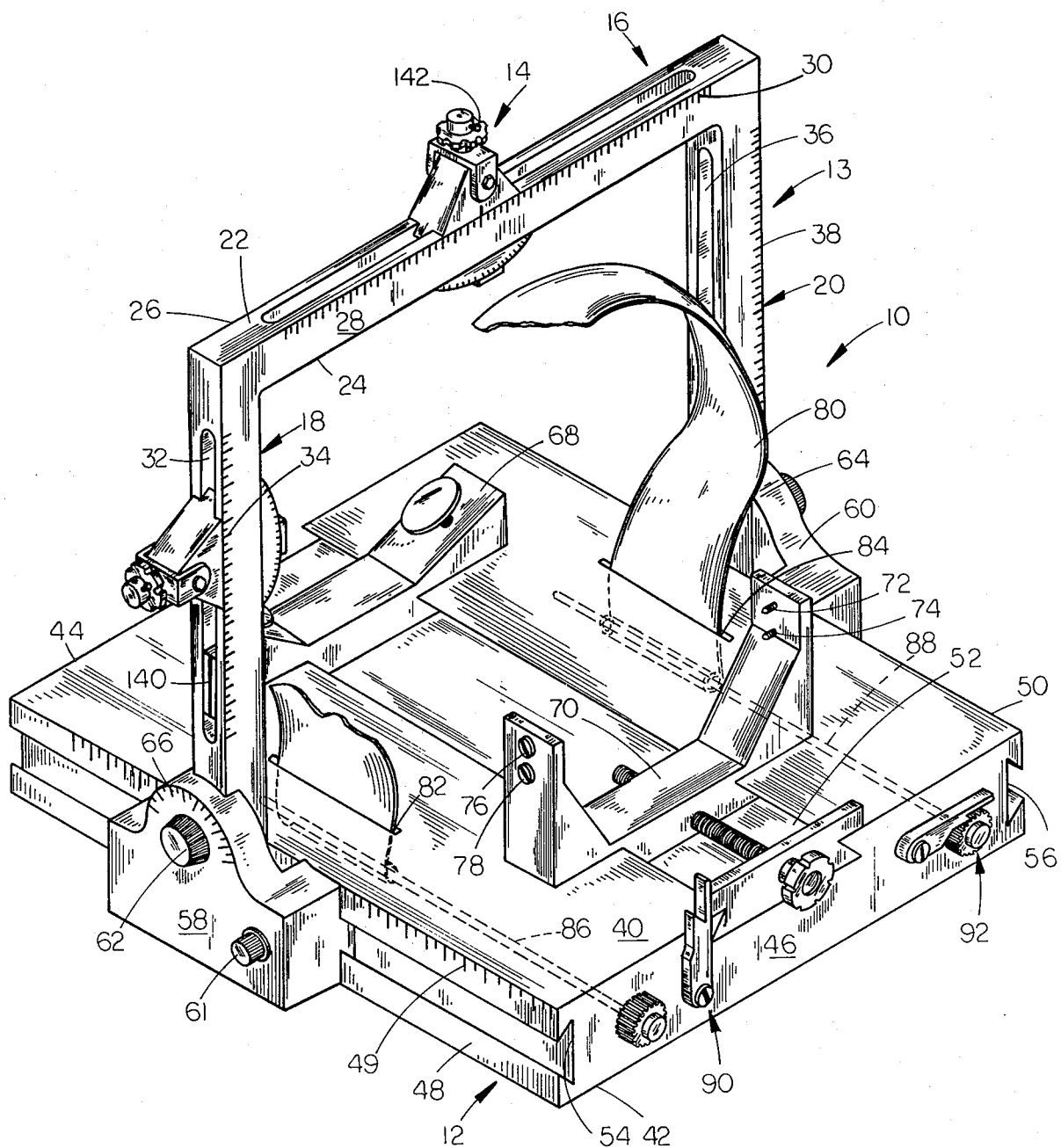
FIG. 1 is a perspective view of the stereotactic frame of this invention.
Figure 3:
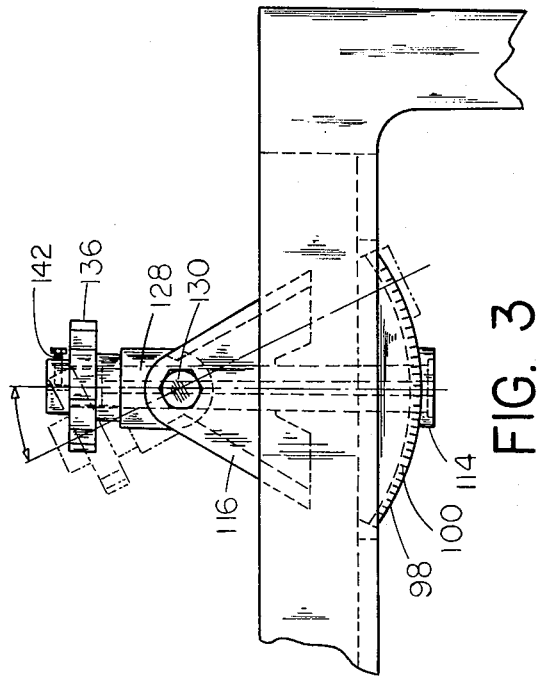
FIG. 3 is an elevational view of the probe holder with the broken lines illustrating an alternate position of the probe holder.
Figure 4:
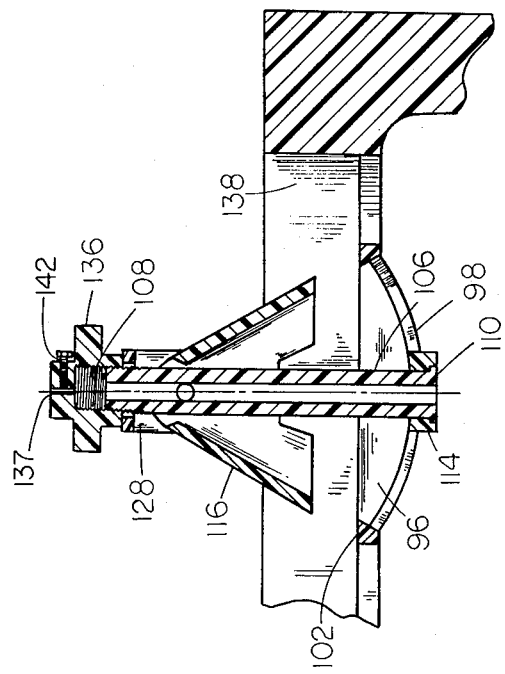
FIG. 4 is a sectional view of the probe holder.

A stereotactic frame is described which is designed for use with a CT Scanner. The frame includes a platform or support means including means thereon for supporting the patient's head and for maintaining the patient's head in position. An inverted substantially U-shaped frame means is selectively movably mounted on the support. A probe holder means is selectively movably mounted on either of the leg portions or the base portion of the frame means and is designed to permit a twist drill bit to be extended therethrough or the probe.

DESCRIPTION OF THE PREFERRED EMBODIMENT

The computed or computerized tomography stereotactic frame of this invention is referred to generally by the reference numeral 10 and includes support means or platform 12 having an inverted substantially U-shaped frame means 13 movably mounted thereon as will be described in more detail hereinafter. A probe holder 14 is selectively movably mounted on the frame means 13 as will also be described in more detail hereinafter.

Frame means 13 is generally U-shaped and includes an elongated base portion 16 having leg portions 18 and 20 extending downwardly from the opposite ends thereof. For purposes of description, base portion 16 will be described as having an upper end 22, lower end 24, and opposite sides 26 and 28. As seen in FIG. 1, side 28 is provided with measurement indicia 30 provided thereon extending the length thereof.

Leg portion 18 is provided with an elongated slot or channel 32 formed therein and it can be seen in FIG. 1 that leg portion 18 is also provided with measurement indicia 34. Likewise, leg portion 20 is provided with an elongated slot or channel 36 formed therein and measurement indicia 38.

For purposes of description, support means 12 will be described as having a top 40, bottom 42, opposite ends 44 and 46, and opposite sides 48 and 50. As seen in FIG. 1, top 40 is provided with a truncated triangular shaped channel 52 formed therein while sides 48 and 50 are provided with truncated triangular shaped channels 54 and 56 formed therein, respectively. Blocks or support members 58 and 60 are selectively slidably movably mounted in the channels 54 and 56, respectively.

Support means 12 is provided with measurement indicia 49 above the channels 54 and 56 to indicate the position of the support members 58 and 60. The support members 58 and 60 are in frictional engagement with the channels and the sides of the support means to provide a yieldable resistance to movement of the support members 58 and 60. In addition, screw 61 threadably extends through support member 58 for engagement with support means 12 to limit the movement of the support member 58 with respect to the support means 12. Similarly, a plastic screw also extends through support member 60 for engagement with support means 12. The lower ends of leg portions 18 and 20 are selectively pivotally mounted to the support members 58 and 60, respectively, by means of thumb screws 62 and 64, respectively. As seen in FIG. 1, support member 58 is provided with indicia 66 thereon to enable the proper positioning of the leg portion 18 with respect to the support member 58. It should also be noted that support member 60 would have identical indicia provided thereon.

The numeral 68 refers to an adjustable neck support which is selectively slidably mounted in the panel 52 designed to engage the neck of the patient. The numeral 70 refers to a head support which is selectively slidably mounted in the channel 52 designed to support the patient's head. Support 70 is provided with head pins 72 and 74 extending inwardly from one side thereof and head pins 76 and 78 extending inwardly from the other side thereof. Head pins 72, 74, 76 and 78 are selectively threadably mounted in the member 70 and are threadably extended through member 70 to engage the patient's head.

A flexible strap 80 extends upwardly through openings 82 and 84 in support means 12 as best seen in FIG. 1 and is designed to extend around the patient's head to maintain the patient's head in position during the surgical procedure. The ends of strap 80 are secured to rods 86 and 88 which extend outwardly through end 46 of support means 12. Thus, rotation of the rods 86 and 88 cause the strap 80 to be wrapped around the rods and to securely engage the patient's head. A ratchet assembly 90 is provided at the end of rod 86 while a ratchet assembly 92 is provided at the end of rod 88 to prevent rotation of the rods 86 and 88 when the strap 80 has been properly positioned.

Figure 2:
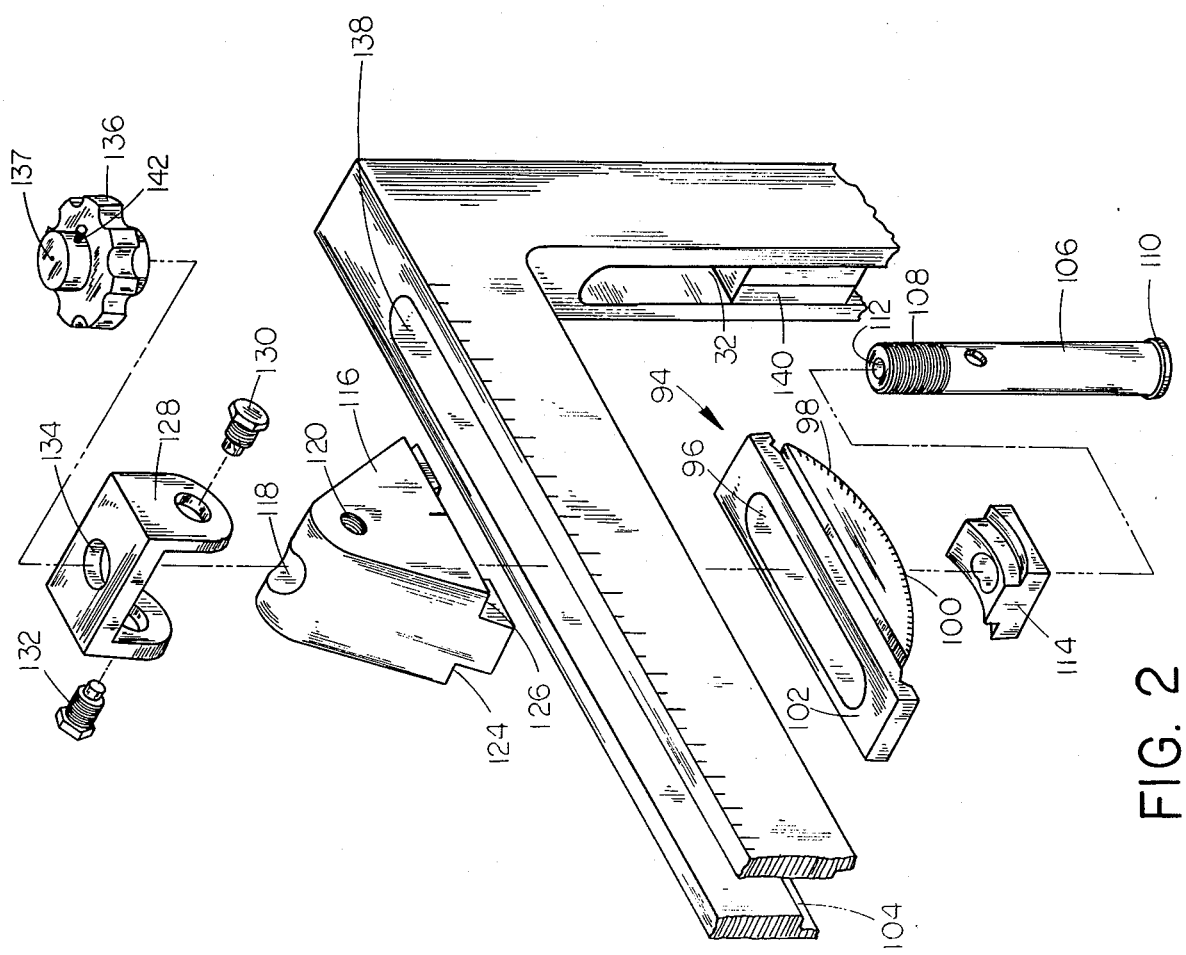
FIG. 2 is a partial exploded perspective view of the probe holder assembly.

Probe holder 14 comprises a lower member 94 having an elongated opening 96 formed therein as best seen in FIG. 2. The lower end of member 94 is arcuate to define a segment-shaped portion 98 having indicia 100 thereon. As seen in FIG. 2, member 94 includes a generally rectangular shaped upper end 102 which is adapted to be received by the channel 104 which is formed in the lower end of base portion 16.

The numeral 106 identifies a tubular member having external threads 108 on its upper end and an enlarged head portion 110 at its lower end. Tubular member 106 is provided with an elongated bore 112 extending therethrough. Tubular member 106 extends upwardly through a washer-like member 114 which engages the lower end of the segment-shaped portion 98 as illustrated.

Probe holder 14 also includes an upper member 116 having a bore 118 extending vertically therethrough and threaded openings 120 and 122 (not shown) extending inwardly thereinto from the opposite sides thereof. Member 116 has a pair of spaced-apart shoulders 124 and 126 which are adapted to engage the upper end of base portion 16 as best seen in FIG. 1. An inverted U-shaped bracket 128 is pivotally mounted on member 116 by means of studs 130 and 132 and is provided with an opening 134 extending through its upper end. As seen in the drawings, tubular member 106 extends upwardly through the opening in the member 114 and through opening 96 of member 94. Tubular member 106 also extends through bore 118 of member 116 and through opening 134 in the bracket 128. Hand wheel or nut 136 is threadably mounted on the upper end of tubular member 106. When hand wheel 136 is loosely threadably mounted on tubular member 106, the probe holder may be slidably moved in the opening 138 formed in portion 16 to the desired position. Additionally, with the hand wheel 136 loosely mounted on tubular member 106, bracket 128, tubular member 106 and washer-like member 114 may be pivotally moved with respect to the members 94 and 116. When the probe holder 14 has been positioned in the desired orientation, hand wheel 136 is tightened which causes tubular member 106 to force the washer-like member 114 upwardly against the lower end of member 94 and to draw the member 116 into frictional engagement with the upper end of the base portion 16 to firmly position the probe holder relative to the frame means.

It should be noted that the probe holder 14 may be mounted on either of the leg portions 32 and 38 to provide additional versatility to the apparatus. As seen in FIG. 1, a laser alignment indicator block 140 is received by the channel 32 in leg portion 34 to enable the frame means 13 to be aligned with the laser beam alignment during the scanning operation. Block 140 may also be secured in channel 36, if desired.

The method of using the frame is as follows. The patient's head is positioned on the head support 70 and the strap 80 is secured as previously described. Screws 72, 74, 76 and 78 are then tightened to further secure the head. The frame means 13 can be slidably moved on the support means 12 and the leg portions 18 and 20 inclined to the desired angle so that the frame means 13 will be brought into the same plane in which the CT Scanner has localized the target with the help of the laser beam of the scanner which is made to align with the line on the middle of indicator block 140. As the apparatus is made of plastic, it may be used in the same CT Scan plane as the target making the solid corners of the frame visible on the scanner, direct measurements can be obtained from the scanner so that the probe holder can be directed towards the target either perpendicular to the frame or at any desired angle. After checking the position of the probe holder on the scanner, a twist drill bit is extended downwardly through opening 137 in hand wheel 136 and through the bore 112 in tubular member 106. The twist drill bit is then employed to drill a hole in the skull. A conventional probe may then be extended downwardly through the probe holder to enable the target to be probed. Screw 142 may be employed to limit the movement of the probe relative to the probe holder. The position of the probe may be confirmed by the scanner.

Thus it can be seen that the frame of the invention described herein employs the principle of working within the plane of the CT Scanner which enables one to obtain direct measurements from the scanner without any alteration of the scanner. Although the apparatus of this invention has been described as being particularly useful to probe lesions within a patient's head, it should be understood that the frame could be slightly modified to enable other portions of the patient's anatomy to be positioned within the frame. Therefore, it can be seen that the apparatus of this invention accomplishes at least all of its stated objectives.

I claim:

1. A computed tomography oriented stereotactic frame, comprising,
    a substantially flat, horizontally disposed support means for supporting a patient's head thereon, said support means comprising a plate including top and bottom portions, opposite sides, and opposite ends,
    said top portion being adapted to support the backside of a patient's head, a support member selectively longitudinally slidably mounted at each of the sides of said support means,
    a frame means comprising first and second leg portions selectively pivotally secured to said support members and extending upwardly therefrom, and a base portion extending between the upper ends of said leg portions,
    said leg portions and said base portion having outer edge portions which are visible on a scanning apparatus, a head support member and neck support member mounted on said support means, a flexible strap means mounted on said support means for securing a patient's head to the support means,
    and a probe holder means selectively movably mounted on said frame means positioned within the plane of the frame means.

2. The computed tomography oriented stereotactic frame of claim 1 wherein said head support member and said neck support member are selectively longitudinally movably mounted on said support means.

3. The computed tomography oriented stereotactic frame of claim 2 wherein said flexible strap means has its opposite ends length adjustably secured to said support means.

4. The computed tomography oriented stereotactic frame of claim 1 wherein said probe holder means may be selectively movably mounted on either of said leg portions or said base portion.

5. The computed tomography oriented stereotactic frame of claim 4 wherein said base portion and said leg portions have measurement indicia provided thereon.

6. The computed tomography oriented stereotactic frame of claim 1 wherein said base portion has upper and lower ends, said probe holder means comprising a first member which is positioned adjacent the lower end of said base portion, a second member positioned adjacent the upper end of said base portion, a hollow tubular member having upper and lower ends and extending upwardly through said first and second members, said tubular member being selectively pivotally received by said first and second members, the upper end of said tubular member having external threads provided thereon, and a threaded member threadably received on the upper end of said tubular member for selectively maintaining said probe holder means in various positions relative to said base portion and for selectively maintaining said tubular member in various pivotal positions relative to said probe holder means.

7. The computed tomography oriented stereotactic frame of claim 6 wherein the lower end of said first member of said probe holder means defines an arc-like configuration and has angle indicia provided thereon.

8. The computed tomography oriented stereotactic frame of claim 1 wherein at least one of said leg portions has an elongated slot formed therein, and a laser beam alignment member mounted in said slot.

* * * * *